(12) United States Patent
Alber et al.

(10) Patent No.: US 8,507,087 B2
(45) Date of Patent: Aug. 13, 2013

(54) MULTI-PURPOSE ITEM REST

(75) Inventors: John Alber, Vero Beach, FL (US); Stanley R Kellenberger, Appleton, WI (US)

(73) Assignee: E4 Technologies, Inc., Vero Beach, FL (US)

( * ) Notice: Subject to any disclaimer, the term of this patent is extended or adjusted under 35 U.S.C. 154(b) by 303 days.

(21) Appl. No.: 12/869,126

(22) Filed: Aug. 26, 2010

(65) Prior Publication Data
US 2011/0052653 A1    Mar. 3, 2011

Related U.S. Application Data

(60) Provisional application No. 61/236,931, filed on Aug. 26, 2009.

(51) Int. Cl.
*B32B 7/12* (2006.01)
*B32B 15/04* (2006.01)

(52) U.S. Cl.
USPC .................... 428/343; 428/354; 428/355 R

(58) Field of Classification Search
USPC .......................................... 428/343, 354, 355
See application file for complete search history.

(56) References Cited

U.S. PATENT DOCUMENTS

| | | | |
|---|---|---|---|
| 2,856,727 A | 10/1958 | Tolbert | 45/68.4 |
| 3,978,553 A | 9/1976 | Honig | 24/7 |
| 4,800,108 A | 1/1989 | Swartz | 428/43 |
| 5,073,457 A | 12/1991 | Blackwell | 428/484 |
| 5,998,308 A | 12/1999 | Cohen | 442/110 |
| 6,644,498 B1 | 11/2003 | Lemberger et al. | 221/33 |
| 7,152,280 B1 | 12/2006 | Taylor | 24/7 |
| 2008/0060559 A1 | 3/2008 | Holland-Hinrichs | 108/28 |
| 2008/0187709 A1 | 8/2008 | Hester et al. | 428/99 |
| 2010/0044271 A1 | 2/2010 | McMillan | 206/553 |

*Primary Examiner* — Victor Chang
(74) *Attorney, Agent, or Firm* — William Giltinan; C. Douglas McDonald; Carlton Fields, PA

(57) ABSTRACT

A multipurpose item rest having a bottom sheet with a non-absorbent surface with an absorbent pad fixedly attached thereto, an outwardly extending tab integral to the bottom sheet having an adhesive area such that the rest may be formed into a restraining device by applying the adhesive are to the bottom surface of the bottom sheet, and a supply of such item rests comprising one or more continuous strips of rests joined with perforated attachments.

5 Claims, 10 Drawing Sheets

MULTI-PURPOSE ITEM REST

CROSS-REFERENCE TO RELATED APPLICATIONS

This application claims priority from U.S. provisional patent application Ser. No. 61/236,931 filed Aug. 26, 2009, which is herein incorporated by reference in its entirety.

BACKGROUND

Public health and well being offers significant challenges in connection with maintaining bacteria-free surfaces in critical areas. Effective methods and standards for cleaning food preparation and consumption areas and medical treatment areas are difficult to enforce and determination of compliance with such methods via visual inspection can be near impossible in commercial environments. Wiping surfaces and items with towels and disinfectant wipes can often exacerbate those challenges as the towels and wipes can transport contaminants and microorganisms from one surface to another.

Because it is often desirable to place utensils or liquid permeable containment devices which may be reused (such as tea bags) down in a sanitary way, napkins, tissues, towels, and the like, have sometimes been used to address sanitary challenges. Such items, however, are not designed primarily to create a sanitary rest and, when used in that manner, are not available for the purposes for which they were designed. Furthermore, when items such as eating utensils, teabags, syringes and the like are laid down, spillage may occur. Napkins, towels, tissues and the like are not designed to contain this type of spillage in a sanitary manner, as is generally desirable both for general cleanliness, and to lessen the risk of spreading infections.

The present invention seeks to address such limitations by providing a multi-purpose rest that is adapted to provide an absorbent and protective resting place that serves as a barrier between potentially unsanitary surfaces and items such as utensils, liquid permeable containment devices, and medical instruments. Additional utility is gained by forming such rests so that they may be used as a restraining device (such as a napkin ring) during distribution and then as a rest thereafter. Still further utility is provided by forming such rests in a manner in which supplies of such rests may be manufactured for use in environments such as commercial kitchens where a substantial number of rests will be needed over a given period of time.

SUMMARY

Disclosed are an absorbent item rest and supplies thereof. The absorbent item rest may conveniently be suitable to absorb liquids having a broad range of viscosities (such as water, coffee, blood, soup, butter, and the like), which are commonly released from food utensils and liquid permeable containment devices such as used teabags and the like. Combining a paper-like bottom sheet and a sanitary absorbent pad attached to that bottom sheet provides a protective, and preferably antibacterial, surface on which to rest utensils or other items, thereby reducing the risk of the utensil or other item coming into contact with un-sanitized surface such as tables, trays, and the like. By incorporating a tab with an adhesive area extending from one side of the rest, the multipurpose rest may also be used as a napkin ring and, when removed, as an item rest.

Supplies of item rests are also disclosed. By forming item rests in one or more continuous strips with perforations between adjacent rests, a supply of rests may be created that conveniently allows for individual rests to be removed as needed. Such supplies are particularly convenient for use in restaurants and similar commercial environments where a substantial number of disposable rests are needed over a given period of time.

Rests according to embodiments of the present invention are suitable for use in environments including, but not limited to, hospitals, restaurants, outdoor eating areas, public and private meeting places, and private residences.

BRIEF DESCRIPTION OF THE DRAWINGS

Other features of the invention will become apparent from the attached drawings, which illustrate certain preferred embodiments, wherein.

DESCRIPTION

Preferred embodiments of the present invention are herein described with reference to FIGS. 1-10. While the following describes preferred embodiments of this invention, it is to be understood that this description is to be considered only as illustrative of the principles of the invention and is not to be limitative thereof, as numerous other variations, all within the scope of the invention as claimed, will be readily apparent to those of skill in the art. The term "adapted" as used herein shall mean sized, shaped, configured, dimensioned, oriented and arranged as appropriate.

Figure 1:
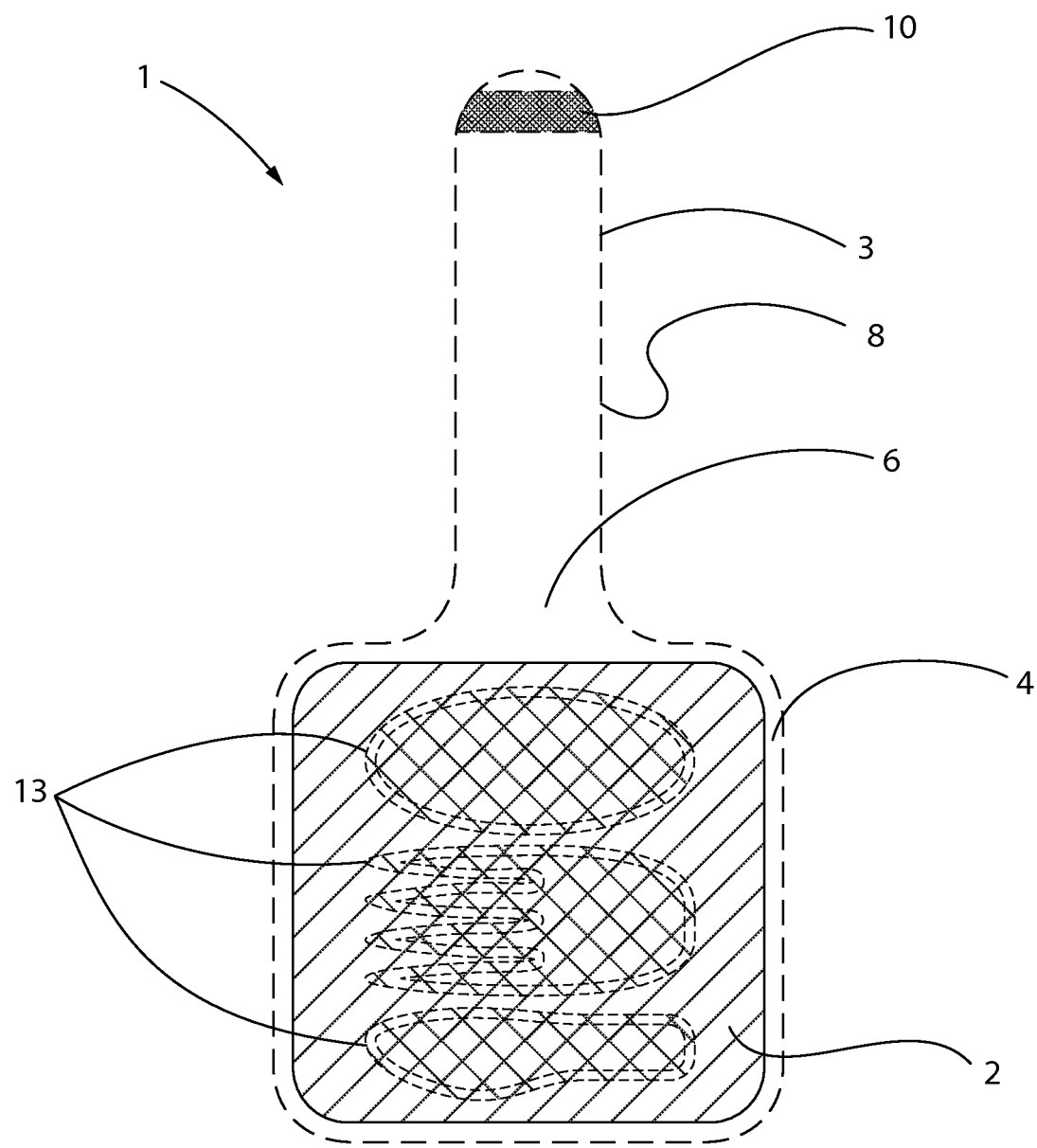
FIG. 1 is a planar view of an embodiment of the rest of the present invention adapted for use with food utensils and as a napkin ring.
Figure 2:
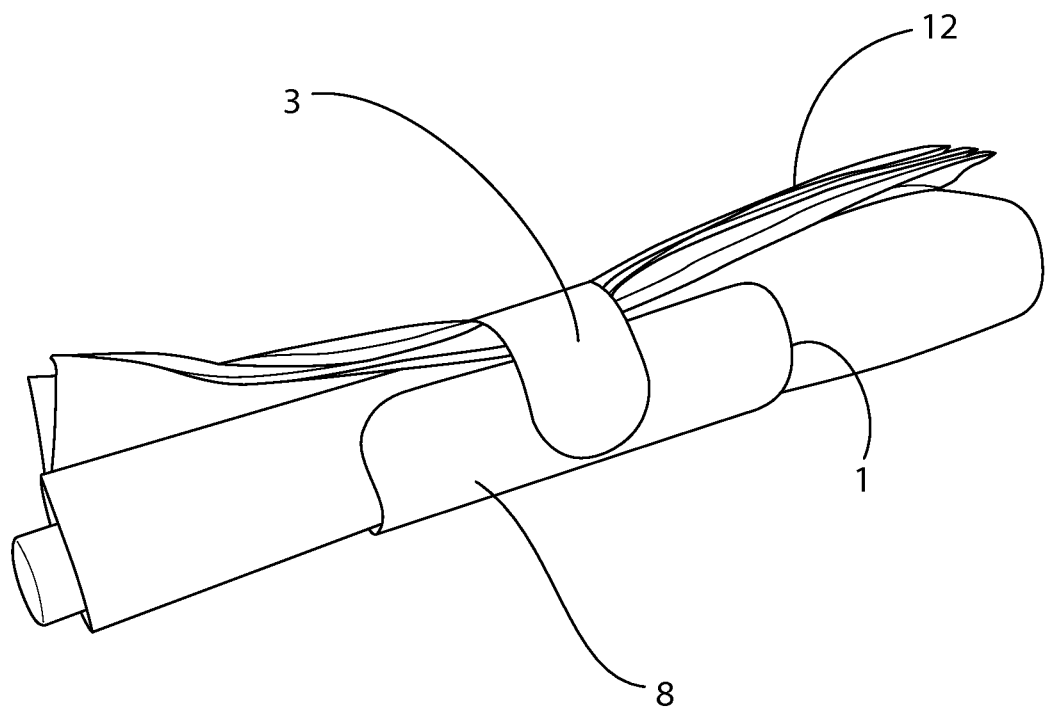
FIG. 2 is a perspective view of the embodiment illustrated in FIG. 1 serving as a napkin ring.

FIGS. 1 and 2 illustrate a preferred embodiment of the item rest 1 of the present invention, adapted to be formed into a napkin ring initially, and then used as an item rest by detaching at the adhesive area, removing the napkin, and placing items such as eating utensils on the item rest 1. Bottom sheet 4 has a non-absorbent bottom surface 8 that acts as a barrier between a potentially unsanitary surface such as a table, tray, or other surface. Absorbent pad 2 is fixedly attached to top surface 6 of bottom sheet 4 and provides a surface on which items such as utensils and liquid permeable containers (such as tea bags) may rest safely. The absorbent nature of absorbent pad 2 helps prevent liquids remaining on items placed on pad 2 from spilling over onto the underlying surface. Additional absorbent material (not illustrated) or structural features such as ridges or channels (not illustrated) may also be used to provide additional protection against such spillage. Tab 3 is integral to bottom sheet 4 and extends outwardly from one side. Tab 3 comprises adhesive area 10 proximal to its outer end. As shown in FIG. 2, when item rest 1 is wrapped around a napkin 12, adhesive area 10 is brought into contact with bottom surface 8, thereby forming a restraining device for a napkin (i.e. a napkin ring). When adhesive area 10 is released and napkin 12 is removed, rest 1 may be unwrapped to lie flat, thereby allowing it to be used as an item rest by placing items on absorbent pad 2.

Bottom sheet 4 may be formed from any of a wide variety of materials known to those of skill in the art. Examples include, without limitation, food quality paperboards such as Signature Solutions NuBrite LBW033 (8 mil bleached linerboard with basis weight of 33#/3 msf) available from Georgia-Pacific Corporation. Where potentially absorbent materials such as paperboard are used, a moisture barrier may be formed by coating bottom surface 8 with various polymers and poly-laminates known to those of skill in the art. In embodiments such as those shown in FIGS. 1 and 2, which may be wrapped as a restraining device around items such as napkins, flexible materials are preferred. In other embodiments, stiffer materials may be used including heavier paperboards, polystyrene paper, closed cell foam board, and other materials known to those skilled in the art. Where such materials are inherently non-absorbent, no additional barrier coating on bottom surface 8 is needed.

Adhesive area 10 may be formed with any of a wide variety of releasable or repositionable adhesives known in the art including, without limitation, microsphere acrylic adhesives such as TM-55 available from Technicote, Inc. or as used on Post-it Notes as available from 3M Corp., and other low tack pressure sensitive adhesives known to those of skill in the art. Such adhesives are generally considered to be low strength as they allow for detachment without tearing of bottom sheet 4. The same effect can also be achieved by forming adhesive area 10 from a cohesive material and adding a matching section of cohesive material (not illustrated) on bottom surface 8. In such embodiments, when adhesive area 10 is pressed against the bottom sheet cohesive material, the two adhere, thereby allowing the rest to be formed into a restraining device such as a napkin ring. Preferably, adhesive area 10 will be near to the outer end of tab 3, but not actually adjacent to the outer end. In this way a small section of tab 3 may be easily grasped for unwrapping. Keeping such area small reduces the likelihood of the outer end of tab 3 accidently catching on an object and releasing prematurely. Where more secure restraints are needed and ease of unwrapping is less of a concern, however, adhesive area 10 may extend all the way to the outer end of tab 3. A release strip (not illustrated), such as silicone coated paper, may further be conveniently used to prevent contamination or premature adherence of adhesive area 10.

Absorbent pad 2 may also be formed from a variety of materials known to those in the art including without limitation fluff pulp, airlaid non-woven materials (e.g. Airtex 866 available from Georgia-Pacific Corporation), superabsorbent granules or fibers, creped wadding, double re-creped materials (e.g. those available from suppliers including Kimberly-Clark Corporation), and open cell foam. Such materials can be effective at absorbing spills and wicking fluids away from items placed on the pad 2. Absorbent pad 2 may be fixedly attached to top surface 6 of bottom sheet 4 in a variety of ways, including with adhesives known in the art including, without limitation, printed aqueous based adhesives and hot-melt sprayed pressure sensitive adhesives. Absorbent pad 2 is preferably sanitary and may further comprise an antimicrobial substance (not illustrated), thereby further inhibiting the risk of spreading infections. Suitable antimicrobial substances include those available from suppliers such as Aegis Environmental Management, Inc. and Microban International, Ltd, as well as others known in the art. Antimicrobial substances may be applied through a variety of methods including, without limitation, using a flexographic printing press and subsequent curing in an oven or by ultraviolet radiation, or simply by spraying the substance onto absorbent pad 2 during manufacture. Antimicrobial substances may also be incorporated into the materials of which absorbent pad 2 is formed during the manufacturing process of the absorbent material from which absorbent pad 2 is formed. Where item rest 1 is to be used in a restaurant or similar setting, not only is it important that the antimicrobial material be safe for use in contact with eating utensils and the like, it is also preferred that it be adapted so as not to transfer to such utensils during use and/or to be substantially odorless and tasteless in the concentrations utilized. This prevents the use of the rest from detracting from the eating experience.

As is discussed further below, it is possible for item rest 1 to be manufactured such that absorbent pad 2 covers substantially all of top surface 6 of bottom sheet 4. While such embodiments may be easier to manufacture in some settings, it is not necessary as embodiments in which absorbent pad 2 does not cover tab 3, and in which bottom sheet 4 extends beyond absorbent pad 2 on one or more sides are also possible, and can result in lower materials costs or enhanced performance. Such embodiments may also allow for the same absorbent pad 2 to be utilized with different sizes and shapes of bottom sheets 4, thereby providing further flexibility during manufacture. Such embodiments may further provide an area of bottom sheet 4 around absorbent pad 2 having additional absorbent material (not illustrated) or additional structural features such as ridges or depressions (not illustrated) adapted to isolate spills on absorbent pad 2 from reaching the table, tray or other surface supporting the item rest 1.

Absorbent pad 2 may optionally further comprise printing or embossing 13 for aesthetic and other purposes including, without limitation, assisting in the capture of liquid, indicating appropriate locations to rest items, and resisting slippage of items. Embossing absorbent materials is known in the art and is often accomplished by compressing a portion of the absorbent pad 2 so that the surrounding areas are thicker or pressing portions of absorbent pad 2 into cup-like depressions (not illustrated) formed in bottom sheet 4. A further optional enhancement is shown on the embodiment illustrated in FIG. 3 in which a detachable coupon 5' is removably attached to bottom surface 8' of bottom sheet 4' by the use of a coupon adhesive area 11'. In such embodiments, Instant Redeemable Coupons (IRC) (available from suppliers including without limitation RR Donnelley, Diversified Label Images and Franklin Packaging) may be used for bottom sheet 4'. Typical IRC base materials and adhesives may, without limitation, consist of a 1 mil and a 0.5 mil polyester film held together with a peelable, non-pressure sensitive adhesive, with pressure sensitive adhesives used to attach the IRC to an absorbent pad as described above. In this way, item rest 1' may serve not only as a napkin ring and an item rest, but also as a convenient promotional device. A further enhancement would be to print informative or aesthetic material (not illustrated) on bottom surface 8, 8' of bottom sheet 4, 4' prior to the application of a non-absorbent material.

Figure 4:
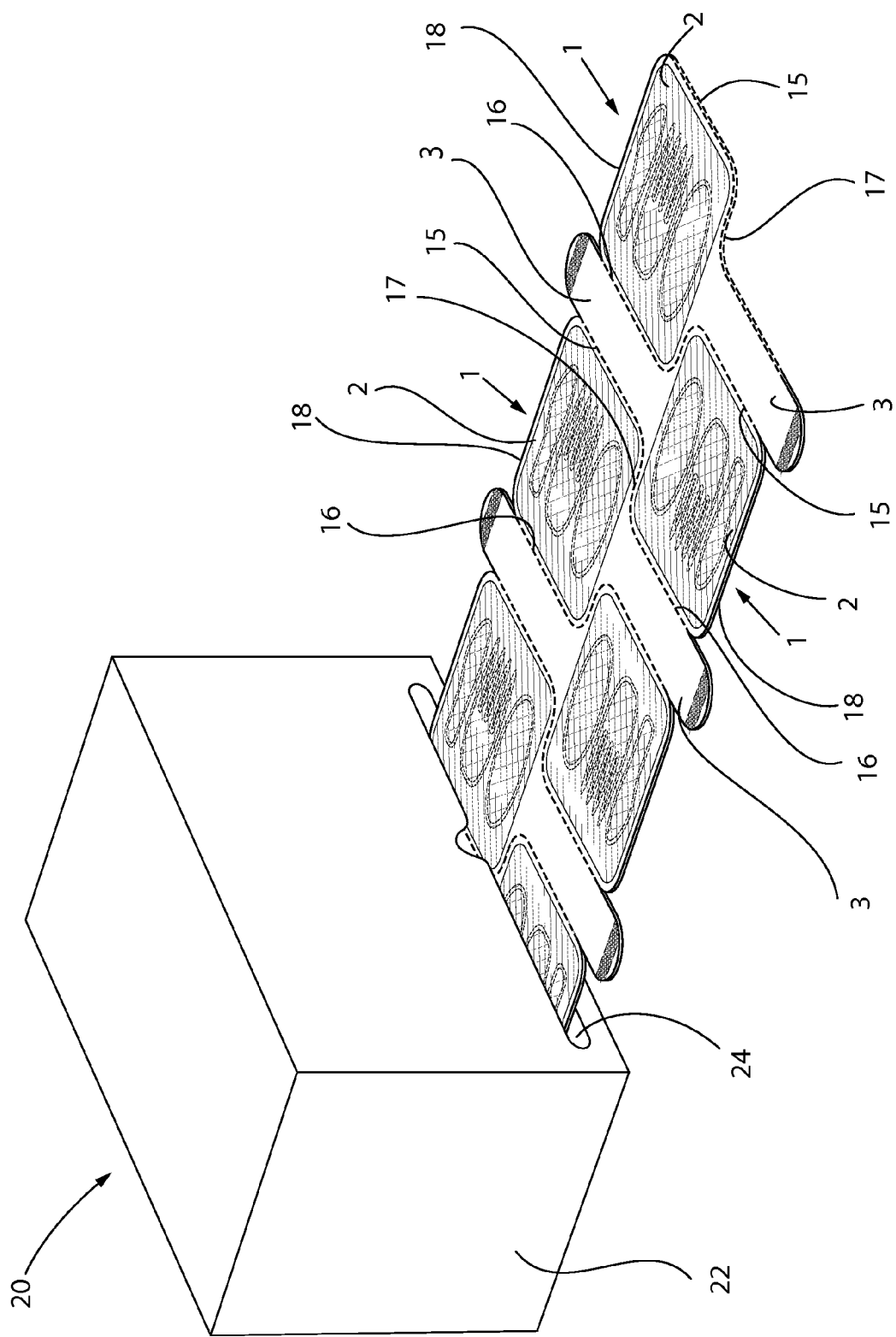
FIG. 4 is a perspective view of a supply of the rests illustrated in FIG. 1.

Having a supply of item rests 1 may be convenient in certain settings, including restaurants and cafeterias. FIG. 4 illustrates an embodiment of such a supply 20 comprising a continuous strip comprising a plurality of item rests 1. Absorbent pad 2 is fixedly attached to a substantially rectangular area having pad portion leading edge 15, pad portion trailing edge 16, pad portion inner edge 17, and pad portion outer edge 18. Pad portion inner edge 17 comprises tab 3 extending in a direction generally opposite pad portion outer edge 18. In this way, a plurality of rests 1 may be formed in a continuous strip with item rests 1 nested such that trailing edge 16 of a first item rest 1 is attached to tab 3 of a second item rest 1, and leading edge 15 of that second item rest 1 is attached to tab 3 of the first item rest. In this way, individual item rests 1 may be torn off the end of the continuous strip as needed. Herein, the terms leading edge and trailing edge are used in reference to strips of item rests in a supply such that a given edge may be a leading edge where a rest in oriented in one direction in such a supply and a trailing edge when oriented in the opposite direction.

Figure 3:
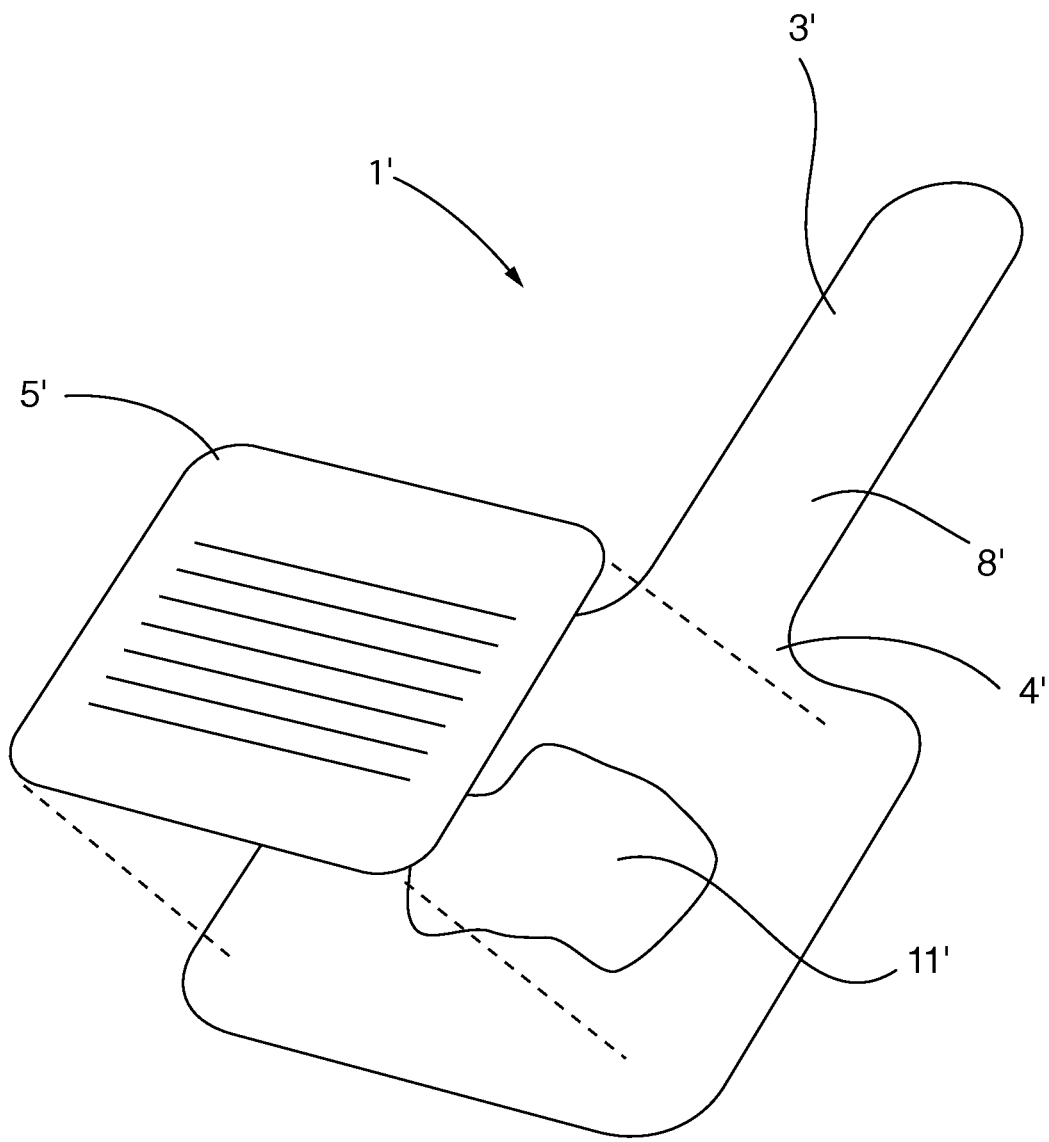
FIG. 3 is a perspective view of an alternate embodiment of the rest of FIG. 1 further comprising a detachable coupon.

The continuous strip of item rests 1 may then be packaged into container 22 having slot 24. Slot 24 is adapted to allow the continuous strip to exit container 22 without exposing the remainder of supply 20 to the outside environment unnecessarily. The manufacture of boxes such as container 22 is well understood in the art. It will be understood that supply 20 may be used in embodiments in which the plurality of item rests 1 includes at least one item rest 1' which further comprises detachable coupon 5' as is shown in FIG. 3. It will be further understood that an additional embodiment of a supply (not illustrated) may be created by stacking unattached rests 1 in a box with a top or bottom opening adapted to facilitate easy removal.

Figure 5:
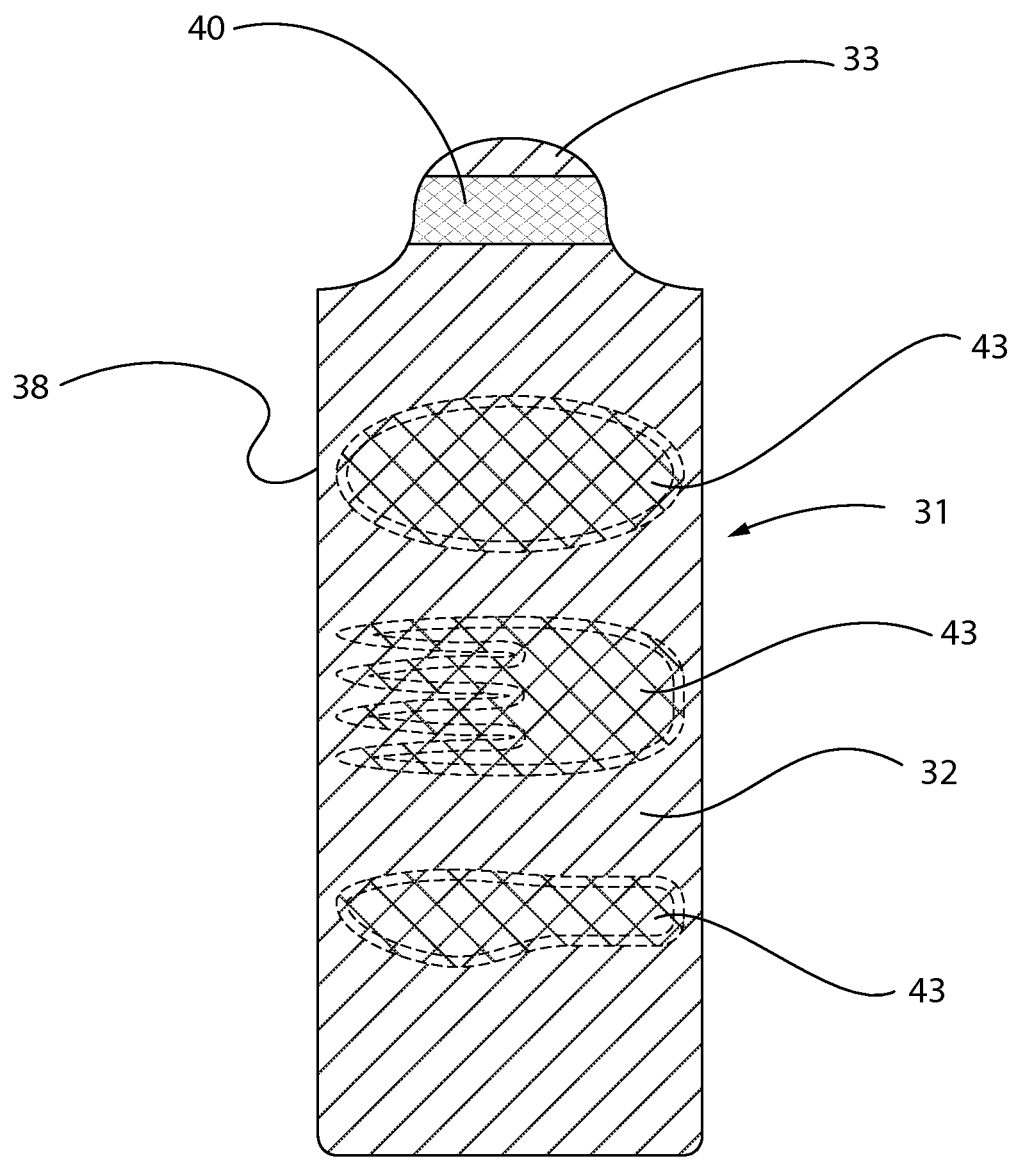
FIG. 5 is a planar view of an alternate embodiment of the rest of the present invention adapted for use with food utensils and as a napkin ring.
Figure 6:
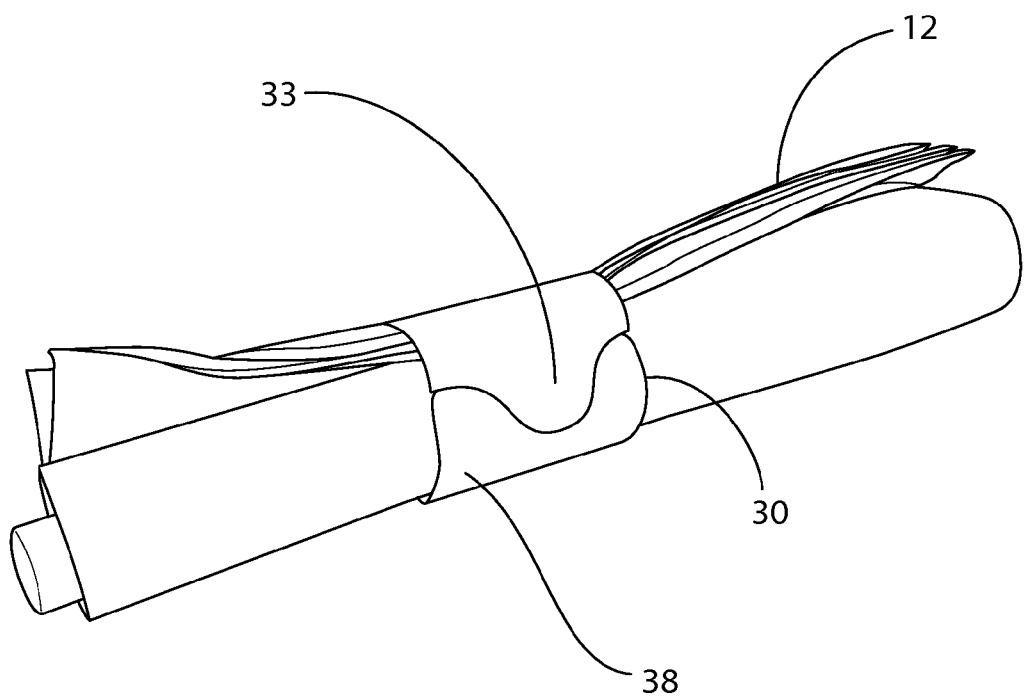
FIG. 6 is a perspective view of the embodiment illustrated in FIG. 5 serving as a napkin ring.

FIGS. 5 and 6 illustrate a further embodiment of the rest 31 of the present invention in which absorbent pad 32 covers substantially all of top surface 36 (shown on FIG. 10) of bottom sheet 34, including the surface of tab 33. In such embodiments, item rests 31 may be manufactured in a process that bonds a continuous strip of absorbent pad 32 material onto a continuous strip of bottom sheet 34 material (illustrated on FIG. 10), thereby eliminating the need to pre-cut sections of absorbent pad 32 material. More specifically, the embodiment illustrated comprises a bottom sheet 34 having a non-absorbent bottom surface 38. Absorbent pad 32 is fixedly attached to the top surface 36 (illustrated on FIG. 10) of bottom sheet 34 with adhesives, bonding, or other similar means known in the art, including those discussed above Adhesive area 40 on absorbent pad 32 is proximal to one edge of rest 31, and allows rest 31 to be formed into a napkin ring (as illustrated in FIG. 6) by wrapping item rest 31 around napkin 12 and bringing adhesive area 40 into contact with bottom surface 38. Item rest 31 may then be used as an item rest by detaching adhesive area 40, removing napkin 12 and placing items such as eating utensils on absorbent pad 32. When optional tab 33 is utilized, adhesive area 40 may conveniently extend across all or part of tab 33. To allow for easier removal, it is preferred to have a small space between adhesive area 40 and an edge of item rest 31 (or tab 33 as appropriate), in order to allow the end to be grasped more easily for detachment.

The same materials described in connection with the embodiments illustrated in FIGS. 1-2 may be used in manufacturing the embodiment illustrated in FIGS. 5 and 6. As with the previous embodiments, bottom surface 38 is non-absorbent and acts as a barrier between absorbent pad 32 and an underlying, potentially unsanitary surface. Absorbent pad 32 provides a clean and preferably sanitary surface for resting items such as eating utensils and liquid permeable containers. For additional protection, absorbent pad 32 may further comprise an antimicrobial substance as was also described above.

Absorbent pad 32 may also optionally include embossed areas 43, which may be formed in the same manner as described above.

Figure 7:
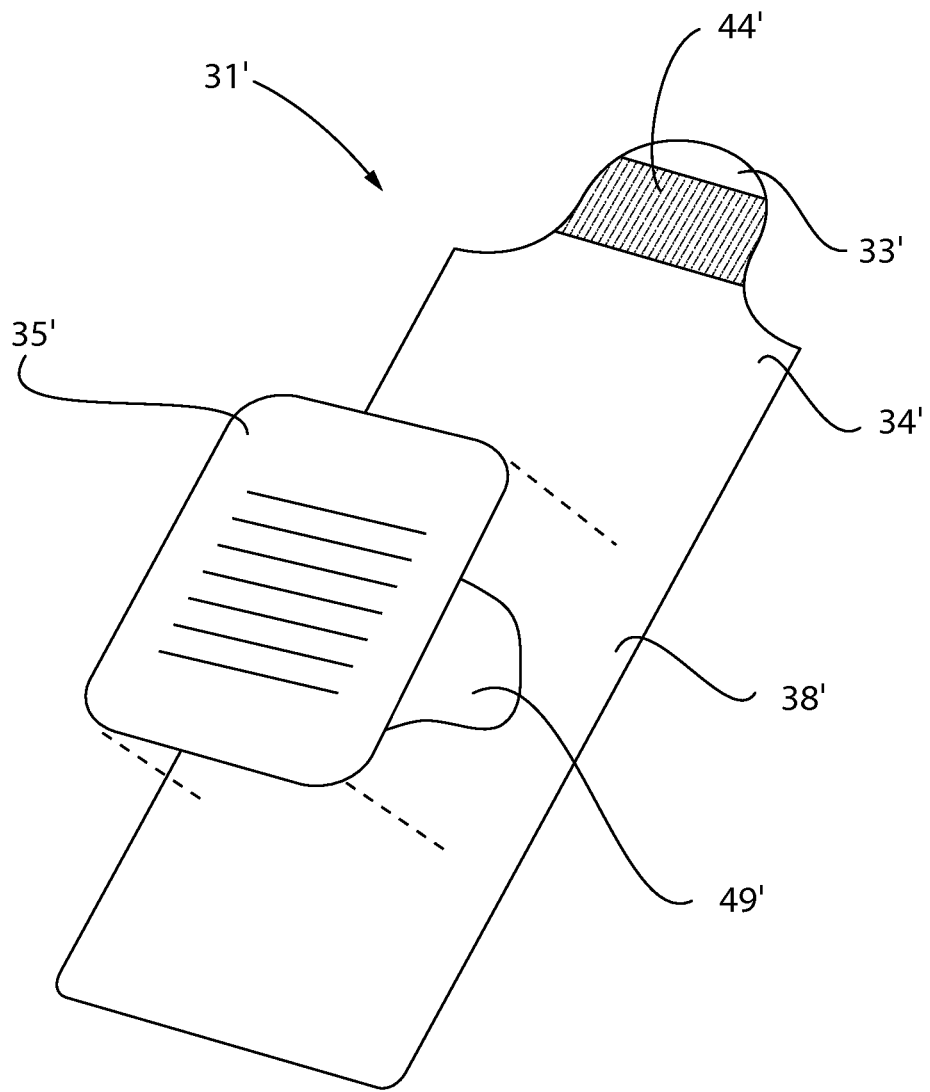
FIG. 7 is a perspective view of an alternate embodiment of the rest illustrated in FIG. 5 further comprising a detachable coupon.

As illustrated in FIG. 7, an alternate embodiment of item rest 31' further comprises releasably attached coupon 35' which may conveniently be attached to bottom surface 38' of bottom sheet 34' with a low strength adhesive or cohesive applied, for example to coupon adhesive area 49'. In this way, item rests 31' may serve a further purpose as a promotional item. Coupon 35' could, as well, serve a similar informational purpose by including instructions or facts potentially of interest to users of item rest 31'. As discussed in the description of the embodiment illustrated in FIG. 3, IRC base may be used for bottom sheet 34'.

Figure 8:
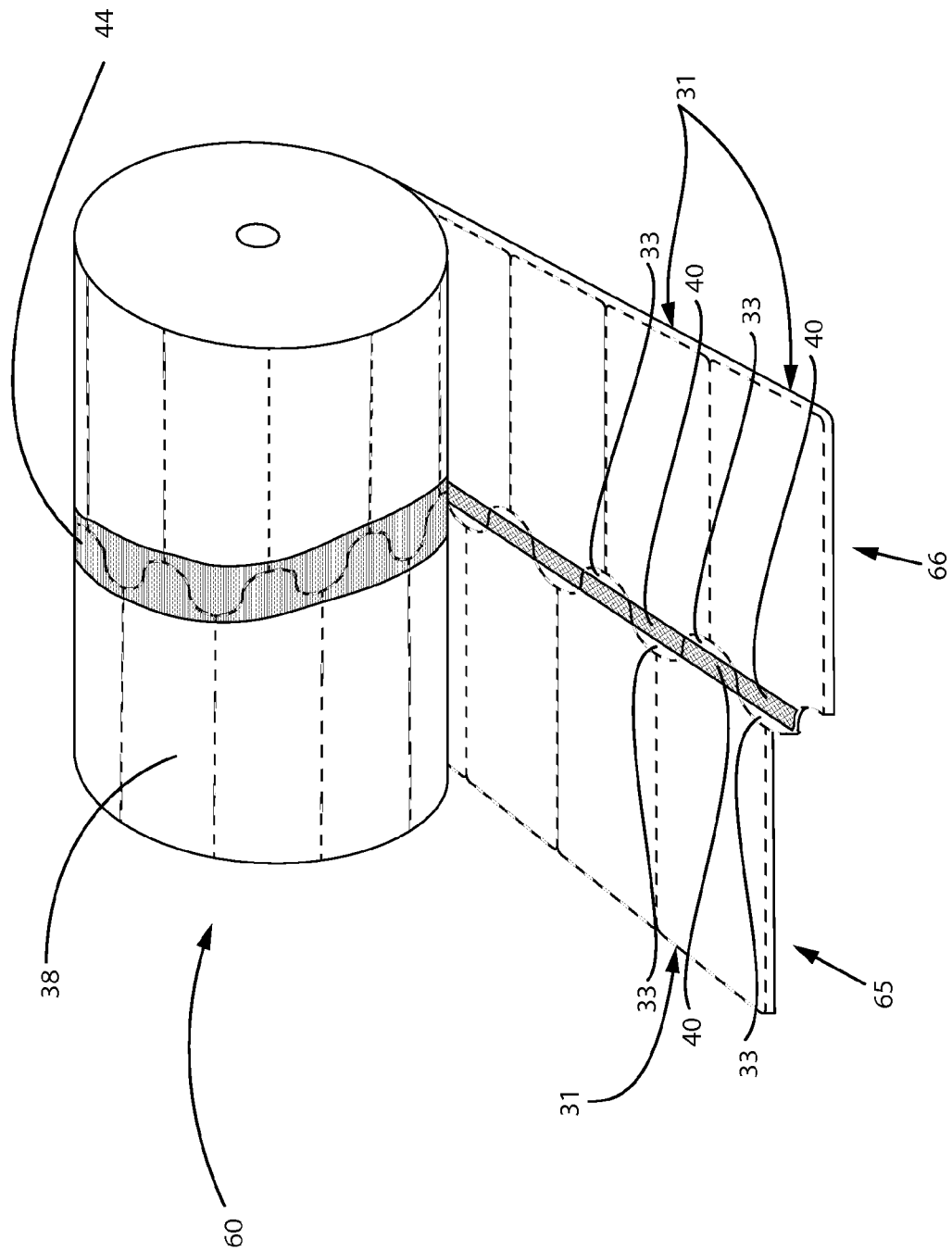
FIG. 8 is a perspective view of a supply of the rests illustrated in FIG. 5.
Figure 9:
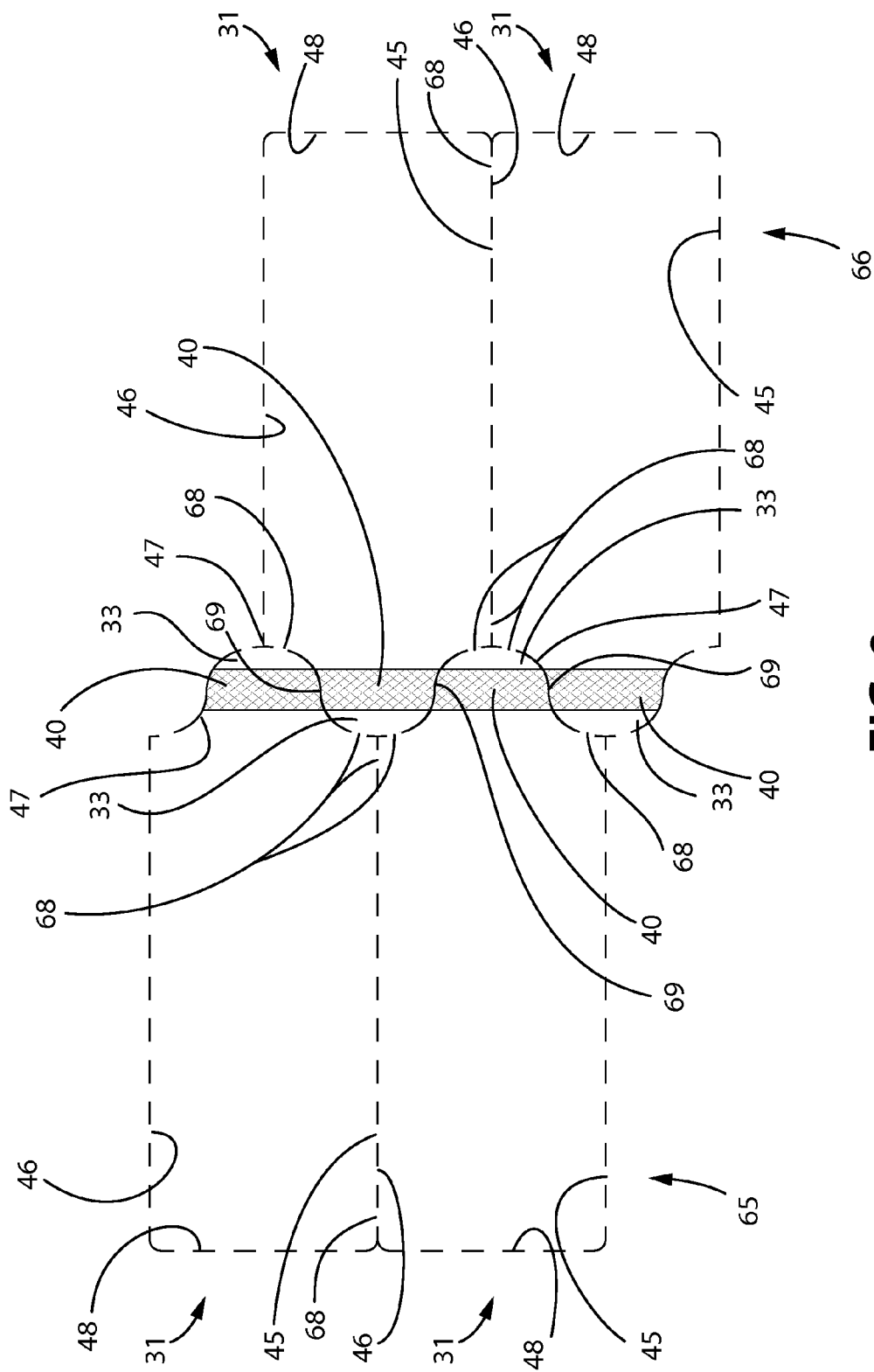
FIG. 9 is a planar view of a section of the supply illustrated in FIG. 8.
Figure 10:
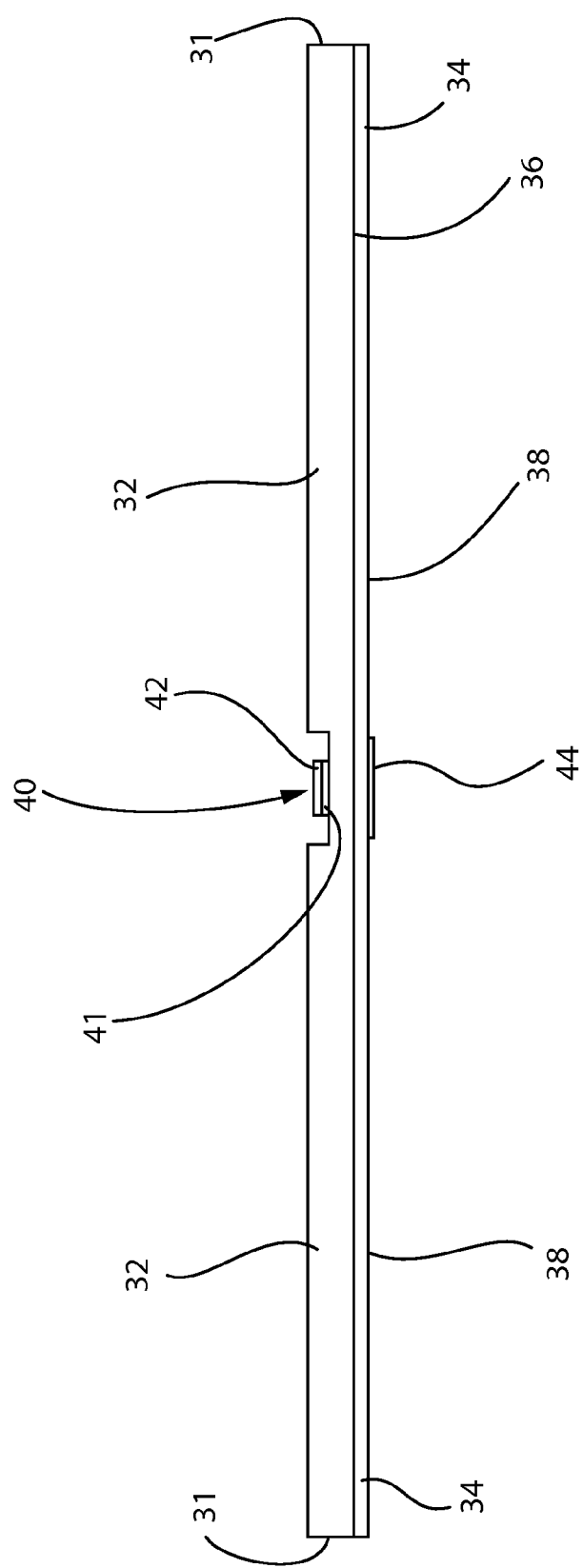
FIG. 10 is an end view of an embodiment of the supply illustrated in FIG. 8.

A supply of item rests 31 is illustrated in FIGS. 8-10. A first continuous strip 65 and a second continuous strip 66 each comprise a plurality of item rests 31. FIG. 9 illustrates a section of supply 60. First continuous strip 65 and second continuous strip 66 each comprise a plurality of item rests 31 with perforated attachments between leading edges 45 of and trailing edges 46 of adjacent item rests 31. First continuous strip 65 and second continuous strip 66 are attached to one another such that tabs 33 are adjacent and, preferably nested, as shown in FIGS. 8 and 9. As illustrated in FIG. 9, in such embodiments item rests 31 comprise leading edge 45, trailing edge 46, outer edge 48 and inner edge 47, which preferably comprises tab 33 extending in a direction substantially opposite outer edge 48. Adhesive areas 40 may then extend across tabs 33 in a preferably discontinuous strip substantially down the center of supply 60.

Although many configurations of perforated attachments may be used, as will be readily apparent to those of skill in the art, it is preferred that attachment points 68 (meaning the points at which adjacent item rests 31 are connected), preferably include attachment points 68 proximal to each corner of item rest 31 and proximal to, but not within, adhesive area 40. In the case of such perforated attachments 68, and without limitation to other parts of the embodiments described, proximal means between about 1 mm and 10 mm, with distances between 2 mm and 8 mm being preferred. As has been noted, it is preferred, but not required, that no attachment points occur in perforation 69 extending across adhesive area 40. In this way, adjacent adhesive areas 40 are discontinuous between adjacent tabs 33. This may be accomplished during manufacture by applying a continuous strip of adhesive and then cutting between adjacent adhesive areas 40 such that the perforations penetrate completely through adhesive area 40, absorbent pad 32 and bottom sheet 34. Alternatively, adhesive material could be applied discontinuously into adhesive areas 40, depending in part on the viscosity and other characteristics of the adhesive material chosen as well as the adhesive dispensing equipment capability. As has been described, leading edge 45 and trailing edge 46 are substantially parallel to each other and substantially perpendicular to outer edge 48. The plurality of attachment points 68 preferably comprise at least one attachment point 68 proximal to a corner formed by leading edge 45 and outer edge 48, at least one attachment point 68 proximal to a corner formed by trailing edge 46 and outer edge 48, and two attachment points 68 proximal to adhesive area 40 with adhesive areas 40 being discontinuous between adjacent tabs. Perforated attachments may conveniently be formed by manufacturing supply 60 in a continuous strip and die cutting between attachment points 68.

Referring again to FIG. 8, supply 60 further comprises release material 44 on or integral to bottom surface 38. Release material 44 is adapted such that, when supply 20 is rolled, release material 44 comes into releasable contact with adhesive areas 40. This both protects adhesive areas 40 from contamination, drying and/or oxidation prior to use and also allows for easy unrolling by preventing adhesive areas 40 from prematurely adhering to bottom surface 38 during manufacture, packaging and/or storage, which could in turn cause roll blocking. It is preferred that release material 44 be wider than adhesive areas 40 to ensure full coverage with release material 44 preferably being between 2 mm to 20 mm wider than adhesive areas 40. The width of adhesive areas 40 will vary based on application, but may conveniently range from 2 mm-25 mm in width with 5 mm-10 mm widths being preferred in typical embodiments, such as those illustrated in FIGS. 1 and 5.

Release material 44 may be a coating applied to bottom surface 38 using processes known to those of skill in the art including, without limitation, flexographic or offset printing, or hot melt extrusion. Those of ordinary skill in the art will recognize that a variety of materials may be used for release material 44 including, without limitation, silicon, polytetraflouroethylene and other low surface energy materials. Alternatively, release material 44 could be formed by winding a separate strip of material onto adhesive areas 40 during manufacture. In such embodiments, it is preferred that the release material 44 extend generally about 3 mm beyond the edge of adhesive areas 40 to allow for easier grasping of the release material during use. In such embodiments in which a separate strip of release material 44 is unwound onto adhesive areas 40, the separate strip will not necessarily be attached to bottom surface 38.

It will be apparent that adhesive material in adhesive areas 40 and release material 44 can serve to make supply 60 thicker in the center of the roll. Because of this, it is desirable to have perforated attachments 68 proximal to, and on either side of adhesive areas 40, to keep tabs 33 in place during manufacture and storage, as has been described above. Additionally, and as is shown in FIG. 10, bulges may be avoided by creating an indentation in absorbent pad 32 in the area of adhesive area 40 adapted to receive the adhesive material and release material 44 when rolled. In such embodiments a pressure sensitive adhesive 41, several of which are known in the art, may be applied to adhesive area 40 with a lower strength adhesive 42 over top. When release material 44 disengages from lower strength adhesive 42, pressure sensitive adhesive 41 is available for activation by pressing adhesive area 40 against bottom surface 38 as described above. This provides further protection for adhesive areas 40 prior to use, and helps prevent bulging during the rolling of supply 60 due to substantially uniform thickness.

As is apparent from the foregoing description, and similar to the embodiments described above in connection with FIG. 4, supply 60 allows for easy dispensing of item rests 31 (and if preferred one or more item rests 31') by simply unrolling a portion of supply 60 and tearing away one or more item rests 31 (or 31') which are then ready for use.

It will be understood that item rests 1, 1', 31, 31' of the present invention are not restricted to use in the food services industry. Other sectors, including healthcare providers, can also benefit from the use of multi-purpose item rests 1, 1', 31, 31' with a non-absorbent bottom sheet 4, 4', 34, 34' adapted to serve as a barrier, and a sanitary and preferably antimicrobial absorbent pad 2, 32 to serve as an item rest. In such applications embodiments of item rests such as those illustrated in FIGS. 1-10 could also be used to restrain items such as dressing kits, suture kits, syringes, and the like in the same way as they may be used to restrain napkins and eating utensils. Accordingly, it is understood that the present invention is not limited to item rests 1, 1', 31, 31' for use in any one particular industry, but is instead adaptable for use in a wide range of applications in which a low cost, disposable, multipurpose rest is needed to prevent otherwise clean, sanitary, or sterile items from coming into contact with unsanitary surfaces. Accordingly, although exemplary embodiments of the present invention have been shown and described, it will be appreciated by those skilled in the art that changes might be made in these embodiments without departing from the principles and spirit of the invention, the scope of which is defined in the claims and their equivalents. In particular, many combinations of materials may be used to achieve suitable results including various adhesives, cohesive, absorbent materials and barrier materials. Item rests of the present invention may also be made in a variety of ways. It is not intended that the description of embodiments herein be limiting.

We claim:

1. A combined napkin ring and item rest comprising
a bottom sheet having a top surface, a non-absorbent bottom surface, and an outwardly extending tab,
an absorbent pad fixedly attached to said top surface, said tab comprising an adhesive area on said top surface proximal to the outwardly extending end of said tab,
whereby said combined napkin ring and item rest may be formed into a napkin ring by wrapping said combined napkin ring and item rest around a napkin and bringing said adhesive area into contact with said bottom surface, and may be used as an item rest by detaching said adhesive area, removing said napkin, and placing items on said absorbent pad.

2. The item rest of claim 1 wherein said absorbent pad further comprises an antimicrobial substance.

3. The item rest of claim 1 wherein said adhesive area comprises a tab cohesive and a portion of said bottom surface also comprises a bottom sheet cohesive adapted such that pressing said tab cohesive against said bottom sheet cohesive shall allow forming said rest into a napkin ring.

4. The item rest of claim 1 further comprising a coupon releasably attached to said rest.

5. A combined napkin ring and item rest comprising
a bottom sheet having a top surface, a non-absorbent bottom surface, and an outwardly extending tab,
an absorbent pad having an absorbent pad top side and an absorbent pad bottom side fixedly attached to said top surface of said bottom sheet,
said absorbent pad covering substantially all of said bottom sheet, and
said absorbent pad top side comprising an adhesive area proximal to the outwardly extending end of said tab,
whereby said combined napkin ring and item rest may be formed into a napkin ring by wrapping said combined napkin ring and item rest around a napkin and bringing said adhesive area into contact with said bottom surface, and may be used as an item rest by detaching said adhesive area, removing said napkin, and placing items on said absorbent pad.

\* \* \* \* \*